United States Patent
Schärer et al.

(10) Patent No.: US 9,613,414 B2
(45) Date of Patent: Apr. 4, 2017

(54) METHOD AND SYSTEM FOR INSPECTING OBJECTS PROVIDED WITH A GAS-BARRIER LAYER

(71) Applicant: FINATEC HOLDING AG, Brügg B. Biel (CH)

(72) Inventors: Matthias Schärer, Aarberg (CH); Bernhard Kubalek, Moosseedorf (CH); Fridolin Maibach, Nidau (CH); Matthias Hermle, Brügg (CH)

(73) Assignee: Finatec Holding AG, Brügg B. Biel (CH)

( * ) Notice: Subject to any disclaimer, the term of this patent is extended or adjusted under 35 U.S.C. 154(b) by 313 days.

(21) Appl. No.: 14/304,053

(22) PCT Filed: Dec. 13, 2012

(86) PCT No.: PCT/EP2012/075369
§ 371 (c)(1),
(2) Date: Jun. 13, 2014

(87) PCT Pub. No.: WO2013/087762
PCT Pub. Date: Jun. 20, 2013

(65) Prior Publication Data
US 2015/0049182 A1   Feb. 19, 2015

(30) Foreign Application Priority Data

Dec. 15, 2011   (EP) ..................................... 11193830
May 16, 2012   (EP) ..................................... 12168391

(51) Int. Cl.
*G06T 7/00*   (2006.01)
*G01N 21/88*   (2006.01)
(Continued)

(52) U.S. Cl.
CPC ....... *G06T 7/0008* (2013.01); *G01N 21/8422* (2013.01); *G01N 21/8803* (2013.01);
(Continued)

(58) Field of Classification Search
None
See application file for complete search history.

(56) References Cited

U.S. PATENT DOCUMENTS

2008/0075329 A1* 3/2008 Brinz ................. B60R 16/0231
382/108
2009/0091050 A1   4/2009 Zelonis
(Continued)

FOREIGN PATENT DOCUMENTS

| JP | 2003 004648 A | 1/2003 |
|---|---|---|
| JP | 2007 256076 A | 10/2007 |
| JP | 2010 032374 A | 2/2010 |

*Primary Examiner* — Kate Luo
(74) *Attorney, Agent, or Firm* — Brinks Gilson & Lione

(57) ABSTRACT

Disclosed are a method and an accompanying system for inspecting objects (5) provided with a gas-barrier layer. The objects have at least one base layer (5a) of a first material, polyethylene or polypropylene, for example, and at least one gas-barrier layer of a different material, EVA or EVOH, for example. An image-recording module (6), such as an infrared camera, records an image of each object (5) and processes the images by means of a processing module (7) in such a way that faulty objects (5) are detected and eliminated. More specifically, the image recording module (6) creates the image of each object (5) within the invisible light spectrum, and the processing module (7) then examines the recorded image, wherein the presence, the absence or the thickness of the gas-barrier layer is determined on the basis of the image.

17 Claims, 2 Drawing Sheets

(51) Int. Cl.
*G01N 21/90* (2006.01)
*H04N 5/33* (2006.01)
*G01N 21/84* (2006.01)
*G01N 25/72* (2006.01)

(52) U.S. Cl.
CPC ....... *G01N 21/909* (2013.01); *G01N 21/9054* (2013.01); *G01N 21/9081* (2013.01); *G01N 25/72* (2013.01); *H04N 5/33* (2013.01); *G01N 2021/8411* (2013.01); *G06T 2207/10048* (2013.01); *G06T 2207/30128* (2013.01)

(56) References Cited

U.S. PATENT DOCUMENTS

2011/0141265 A1\* 6/2011 Holtkamp ............. G01J 5/0003
 348/86
2011/0235672 A1\* 9/2011 Shepard ................. F01D 5/186
 374/45

\* cited by examiner

METHOD AND SYSTEM FOR INSPECTING OBJECTS PROVIDED WITH A GAS-BARRIER LAYER

TECHNICAL FIELD OF THE INVENTION

The present invention relates to a method and a corresponding system for inspecting objects provided with a gas-barrier layer. In particular, the present invention relates to a method and a corresponding system for inspecting objects provided with a gas-barrier layer which consist of at least one base layer of a first material and at least one gas-barrier layer of a different material, wherein an image of each object is recorded by means of an image-recording module and is processed by a processing module in such a manner that faulty objects are detected and eliminated.

BACKGROUND OF THE INVENTION

Fresh drinks (for example fresh milk or pressed fruit juices) are nowadays very often sold in plastics containers. Such containers are frequently in the form of a bottle with an appropriate screw cap. Suitable materials for the production of such plastics containers are in particular polypropylene (PP) or polyethylene (PE), it also being possible to use many other materials such as, for example, PET (polyethylene terephthalate). The same materials are conventionally also used to produce screw caps. In the case of certain other products, cans are provided which are closed by attachable lids which fit onto the opening. Such lids are often referred to as snap-on lids because they form a snap fit with the flange of the container opening.

It is particularly important in the case of such fresh products that they are able to remain in the perfect state from the time of packaging to the time of consumption. It has been shown in particular that contact of the products with oxygen from the ambient air very quickly leads to various reactions and consequently to a negative change in the fresh foodstuffs. Although many of these changes do not actually impair the edibility of the products, they nevertheless lead to a marked change in the taste, smell, colour or consistency, which adversely affects the sale of such products.

Because conventional screw caps for plastics bottles or snap-on lids for cans are typically not air-tight, various measures have already been proposed to ensure that such fresh foodstuffs are sealed in an air-tight manner. One of the most frequently used measures is an air-tight seal of the container opening, which must first be removed prior to consumption. There is typically used for that purpose an aluminium-containing foil, the ends of which are attached in an air-tight manner to the opening of the container by a special soldering process. The container is then closed by the screw cap. However, such an additional foil involves numerous disadvantages, in particular because the packaging process in the case of such containers is made more difficult, and accordingly also more expensive, by the addition of a supplementary step. However, such a closure is also associated with disadvantages for the consumer, because the foodstuffs cannot be consumed before the protective film is removed. In addition, the protection from air is completely eliminated once the protective film has been removed, so that foodstuffs which have not been used up fully can no longer be stored for very long.

Ethylene vinyl alcohol copolymer (EVOH) is a material, or a group of materials, which is extremely suitable for air-tight sealing because it has outstanding gas-barrier properties. In addition, EVOH copolymers are resistant to oils and organic solvents and can additionally be applied very easily to other plastics, with which they form strong composites. These advantageous properties have led to EVOH being used in the packaging industry, especially in the field of medical, pharmaceutical and cosmetic products. In addition, the practice has recently begun of forming either an EVOH coating or an EVOH intermediate layer in the case of screw caps produced from conventional plastics. The reason for this is that such an additional EVOH layer has the effect that containers can be sealed in an air-tight manner using only the cap, as a result of which additional protective films are completely unnecessary. Packaging processes can thus also be simplified, so that the products can be sold substantially more cheaply. Such caps also provide protection against the ambient air even after the containers have been opened, which cannot be ensured in the case of the conventional methods.

However, for reliable air-tight sealing, the EVOH layer must not have any gaps, so that EVOH not only has to be present but also must be free of gaps and faults and have a sufficient layer thickness. This is because gaps in the EVOH layer can lead to the ambient air being able to enter the container despite the seal, as a result of which the above-described problems relating to the change in the fresh products occur. Unfortunately, however, there are at present no satisfactory inspection methods by means of which screw caps with an EVOH layer can be inspected on an industrial scale. The reason for this is that EVOH layers cannot be distinguished visually from the caps, so that the inspection of such coated screw caps with the aid of conventional inspection methods is not possible. For this reason, such caps are unfortunately not widely used.

From WO 2007/021551 A1 there is known a method for determining the authenticity of packaging for pharmaceutical material. These original packagings consist of PP or HDPE and approximately 5% added EVA. In this method, a spectrum of the packaging material is recorded by means of an FTIR spectrometer, and conclusions are drawn from the presence or absence of specific peaks as to the presence or absence of EVA, and accordingly as to an original packaging.

From US 2002/0033943 A1 there is known a method for determining the quality of objects made of coloured plastic, in which a camera operating in visible light and near-infrared is used to detect bubbles, particles or crystalline regions in the wall material or to determine filling levels in dark containers. To that end, the object made of PP, PE or EVOH is irradiated with infrared light of from 700 nm to 2000 nm, and reflected, scattered or unabsorbed light is detected.

SUMMARY OF THE INVENTION

Accordingly, it is an object of the invention to propose a method for inspecting objects provided with a gas-barrier layer and also a system suitable for carrying out the method, in which the disadvantages of the known methods and systems are overcome or at least greatly reduced.

It is a particular object of the invention to provide a method and the corresponding system for inspecting objects provided with a gas-barrier layer, by virtue of which a reliable, quick and simple automatic check is ensured. In addition, the faulty objects are also to be able to be eliminated automatically.

In particular, the objects of the invention are achieved in that, in the method for inspecting objects provided with a gas-barrier layer which consist of at least one base layer of a first material and at least one gas-barrier layer of a second material, wherein an image of each object is recorded by means of an image-recording module and is processed by a processing module in such a manner that faulty objects are detected and eliminated, the image of each object is created by the image-recording module in the invisible light range and the recorded image is examined by the processing module, wherein the presence, the absence or the thickness of the gas-barrier layer is determined on the basis of the image. The invention accordingly uses the wavelength ranges of UV and IR light, which are adjacent to the visible range of the electromagnetic spectrum and in which many materials exhibit different properties, in particular absorption properties, than in visible light.

The particular advantage of this invention is that the objects provided with a gas-barrier layer are subjected to an image inspection in the invisible light range, as a result of which the faults in the gas-barrier layer that are detectable in the invisible light range but are not discernible in visible light can be detected. Because the material of the body (or of the base layer) of the object and the material of the gas-barrier layer typically have the same colour, it is not possible, or is possible only with difficulty and imprecisely, to distinguish them from one another by means of image processing in the visible light range, as indicated above. Analysis in the invisible light range solves this problem and provides a reliable inspection method.

In one embodiment of the present invention, the first material of the base layer and the second material of the gas-barrier layer are chosen in such a manner that they produce different images in the invisible light range. For example, a first material can appear in a first colour in the detected image, while the presence of a different material is represented by a different colour. Regions in which both materials can be found accordingly acquire in the recorded image a colour that is formed, for example, by mixing the other two colours. It is, of course, also readily possible to represent the different layers by the same colour, for example by using different shades of colour, intensities or contrasts. This embodiment has the advantage, inter alia, that the different images of the first material and of the second material in the invisible light range can be used for a simple examination of the presence of the gas-barrier layer. The image-processing algorithms can thus also be kept relatively simple, as a result of which more rapid processing is possible.

In another embodiment of the present invention, the image of the object is examined at predetermined wavelengths, wherein those wavelengths are chosen in dependence on the first material of the body and on the second material of the gas-barrier layer. The particular advantage of this embodiment is that the examination of the image can be reduced to the examination of the predetermined wavelengths, as a result of which even simpler and even more rapid processing is possible. Because it is possible to show that different plastics materials often reflect or absorb different wavelengths in the invisible light range, a very precise distinction can be made between different materials without a very great outlay. Differences in the scattering, reflection and/or absorption behaviour of the two materials of the objects in the UV and/or IR light range are accordingly used to great advantage according to the invention.

In a further embodiment, the image-recording module is a camera that is sensitive in the range of infrared radiation. The particular advantage of this embodiment is that an image of the objects provided with a gas-barrier layer that has been created in the infrared light range can be used. Infrared cameras are used nowadays in various technical fields, so that they have in the meantime become simple and inexpensive to use. In addition, it can be shown that different plastics exhibit very specific absorption and emission properties as well as reflection patterns in particular in the range of infrared radiation, as a result of which the inspection of a gas-barrier layer of a material that differs from the material of the body of the object yields especially good results in that range. Despite higher procurement and operating costs, an IR camera advantageously offers a low exposure time and wavelength specificity as compared with other IR-capable image-recording devices such as microbolometers and accordingly advantageously permits rapid and continuous checking of the objects guided past it. High throughput rates which are particularly valuable economically can thereby be achieved.

In yet another embodiment of the present invention, when a faulty object is detected, that object is eliminated by an elimination module on the basis of a signal from the processing module. The particular advantage of this embodiment is that the faulty objects can be eliminated automatically, which makes the inspection process particularly efficient and inexpensive.

In another embodiment of the present invention, the objects are transported past the image-recording module by a conveyor device in such a manner that an image of each object is recorded. The advantage of this embodiment is, inter alia, that the objects to be inspected can be moved by a conveyor device, while the sensitive elements of the system, such as, for example, the image-recording module, can be stationary. In this manner, on the one hand the likelihood of breakdowns is reduced and on the other hand the precision of the recording of the images of the objects to be inspected is increased.

In one embodiment of the invention it is provided that the conveyor device guides the objects past the image-recording module continuously. In combination with the stationary, rapidly working cooled IR camera, the method according to the invention accordingly permits a high throughput of objects. According to the invention, continuously means especially the flowing transport of individual objects past the lens of the camera in a manner that is uninterrupted in terms of time. Transport in a manner that is interrupted in terms of time but in which the image-recording device is displaced continuously over the objects, which are stationary for a short time, would also be continuous within the meaning of the invention. This embodiment corresponds to the batch-wise processing of a group of objects over which the image-recording device is displaced, while the objects themselves are stationary. Accordingly, non-continuous within the meaning of the invention means only the stopping of the image-recording module from image to image.

Depending on the camera, this transport of the objects takes place in the form of objects which follow one another in series, that is to say linearly. If the camera and software are capable, transport can of course also take place in two or more rows, in which case the stationary or continuously movable camera would record two or more, for example four, objects simultaneously with each image. The arrangement of one camera per row is also in accordance with the invention. The objects arranged in two or more rows can thereby be staggered or arranged in columns. In the first case, the elimination device could remain unchanged; in the second case it would have to be operative in two more or less opposite directions in order to avoid accidentally taking fault-free objects with it when ejecting faulty objects. The transport path of the conveyor device can also contain curves or bends, for example it can be in the form of a turntable. The transport path can have any desired spatial orientation, that is to say it can also be oriented purely vertically, for example, and consequently be in the form of a free-fall or sliding section.

In yet another embodiment of the present invention there is provided an irradiation element by means of which the objects can be irradiated with the infrared radiation. This embodiment has the particular advantage that the objects provided with a gas-barrier layer that are to be inspected are irradiated by an external infrared source, so that the different materials of the base layer and of the gas-barrier layer are able to reflect, scatter or emit absorb that radiation. Because, as already mentioned, different plastics reflect, scatter or absorb different wavelengths in the infrared range, it is very easy to draw a conclusion, on the basis of the wavelengths recorded in the image, as to the presence or absence, or alternatively the thickness, of the gas-barrier layer. By adjusting the radiation intensity, the different shapes or dimensions of the coated objects to be inspected can also very easily be taken into account.

In another embodiment of the present invention there is provided a heating element by means of which the objects are heated in such a manner that they develop a characteristic radiation in the infrared range. The heating element can be used instead of the irradiation element or together with the irradiation element. The particular advantage of this embodiment of the present invention is that the characteristic radiation of the objects provided with a gas-barrier layer can be used to record the image thereof. In this case, for recording the IR radiation emitted by the objects, the method according to the invention also uses a bolometer, in particular a microbolometer, as an alternative or in addition to the IR camera. Because the infrared radiation corresponds substantially to the thermal radiation, different temperatures of the bodies can be recorded by a corresponding recording unit. Because it can be shown that different plastics heat up at different rates when heated for a limited time, it is easy to understand that they also produce different thermal images. By virtue of this property, the different materials can again be distinguished from one another, which can be used for the simple and reliable inspection of objects.

The first material of the base layer of the objects to be inspected can typically be polypropylene and/or polyethylene, while the second material of the gas-barrier layer is typically ethylene vinyl acetate (EVA) and/or ethylene vinyl alcohol copolymer (EVOH). Other suitable materials are, of course, also possible, however, provided they produce a different pattern in the recorded image in the invisible light range.

It should be mentioned at this point that, as well as relating to the described method according to the invention for inspecting objects provided with a gas-barrier layer, the present invention relates also to a corresponding system for inspecting objects provided with a gas-barrier layer.

BRIEF DESCRIPTION OF THE DRAWINGS

Embodiments of the present invention will be described below by means of examples. The examples of the embodiments are illustrated by the following accompanying figures.

DETAILED DESCRIPTION OF THE EMBODIMENTS

Figure 1:
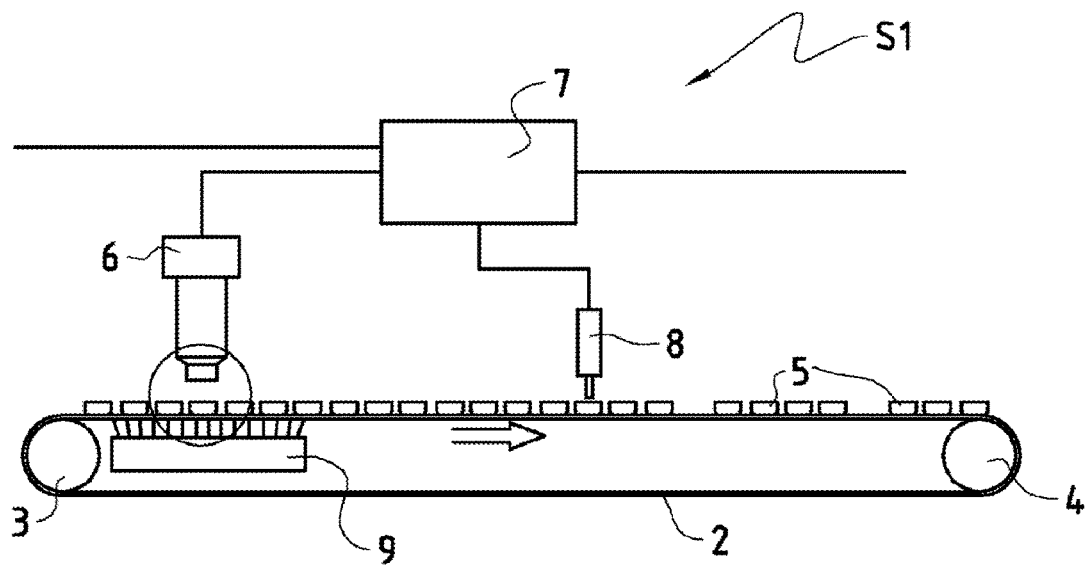
FIG. 1 shows schematically a block-like representation of a system for inspecting objects provided with a gas-barrier layer according to a first embodiment of the present invention, seen from the side.

FIG. 1 shows schematically and in block-like form a system S1 for inspecting objects 5 provided with a gas-barrier layer, which system can be used to carry out the method according to a first variant embodiment of the present invention. The objects 5 to be inspected are typically screw caps made of plastic, by means of which containers for liquids (e.g. bottles) can be closed. However, this invention is of course not limited to such screw caps and it relates equally to many other objects 5 provided with a gas-barrier layer which have a similar structure, for example snap-on lids for cans. It is of course wholly conceivable to inspect objects 5 which are not closing means at all but which are simply required to have good gas-barrier properties.

The system S1 substantially comprises a conveyor device 2 by means of which the objects 5 provided with a gas-barrier layer can be transported. The conveyor device 2 can be in the form of, for example, a conveyor belt with corresponding drive devices 3, 4, on which conveyor belt the objects 5 to be inspected are placed. The conveyor device 2 can also be or have a free-fall section, it can convey the objects in a different contact-free manner, for example by means of compressed air, if possible magnetically or inductively, or it can also hold the objects in a different manner by contact, provided it does not restrict the recording of emission, absorption, scattered or reflected radiation of the objects by the camera. A conventional conveying speed is 80 m/minute, so that, depending on the recording and integration time, approximately 1000 objects are examined per minute. It is particularly advantageous and essential to the invention that the conveyor device 2, irrespective of its configuration, guides the objects 5 past the camera continuously, so that high throughputs are achieved.

The objects 5 can be placed on the conveyor device 2 both manually and by devices suitable therefor. In particular, it is also conceivable to bring the objects 5 provided with a gas-barrier layer that are to be inspected directly from the production plant to the conveyor device 2, so that inspection for faults can take place automatically before they are transported further. In this case, the device according to the invention works in-line with the production plant for the objects.

When the inspection in the system S1 has taken place, the faulty objects 5 provided with a gas-barrier layer are sorted out automatically. To that end there is provided an elimination module 8, which removes the faulty objects 5 from the conveyor device 2. This elimination can take place, for example, by means of a short, purposive blast of compressed air, whereby the faulty objects 5 provided with a gas-barrier layer are blown off the conveyor device 2 and then disposed of or recycled in a suitable manner. It is also possible to provide elimination modules 8 of a different type by means of which the faulty objects 5 provided with a gas-barrier layer can be eliminated. However, requirements in relation to speed, safety and efficiency must be met. Those objects 5 which successfully pass the inspection, on the other hand, are transported further by the conveyor device 2 and then leave the system S1. It is of course possible to provide at the exit from the system S1 devices which transport the inspected objects 5 further, for example into a printing, cleaning or other system. Such further elements are already known, however, and do not impair the present invention. For this reason they are not described in greater detail.

Inspection of the objects 5 provided with a gas-barrier layer in the system S1 takes place in principle as follows: an image of each object 5 is created in the invisible light range, and the recorded image is then examined by means of image recognition software in order to detect faults in the objects 5. The faults which are in particular to be detected relate to the quality of the gas-barrier layer, that is to say especially the presence or absence of the gas-barrier layer 5b, and not least also to the thickness and evenness thereof. A gap-free gas-barrier layer 5b is a significant quality factor in the production of air-tight screw caps 5, for example, for which reason reliable inspection of the coating 5b is extremely important.

The image of each object 5 in the system S1 is created by an image-recording module 6. The image-recording module 6 is typically a cooled IR camera that is sensitive in the range of infrared radiation and the working range of which is at wavelengths of from 1 μm to 14 μm, in particular from 2.5 μm to 5.1 μm. Infrared radiation generally refers to radiation in the spectral range between 780 nm and 1 mm, which corresponds to a frequency range of approximately from 300 GHz to 400 THz. Such cameras are capable of recording different wavelengths that are invisible to the human eye, different wavelengths being represented differently in the recorded image. Because different objects and different materials normally absorb, reflect or scatter, or emit, different wavelengths in the invisible range, the evaluation of an image of an object 5 provided with a gas-barrier layer recorded by the image-recording module 6 can be used to inspect its properties. The camera used in this example has an exposure time of approximately 0.4 ms and permits a resolution of 640×512 pixels and a thermal resolution of <20 mK. The camera can of course also have other resolutions, for example 320×256 pixels, in order to be able to make the exposure time even shorter.

To that end, the image recorded by the image-recording module 6 of the object 5 provided with a gas-barrier layer that is to be inspected is transmitted to a processing module 7, where the evaluation of the image is carried out. There can be used for the evaluation various algorithms which make use of the fact that, as mentioned above, different materials produce images in the invisible light range which can clearly be distinguished from one another. Image recognition software detects the presence, the absence or the thickness of the barrier layer as well as faults in the flow of the plastic, that is to say irregularities within the EVOH or EVA layer. Once a faulty object 5 has been detected by the processing module 7, a control signal is emitted from the processing module 7 to the elimination module 8, as a result of which the defective object 5 can be eliminated.

Figure 3:
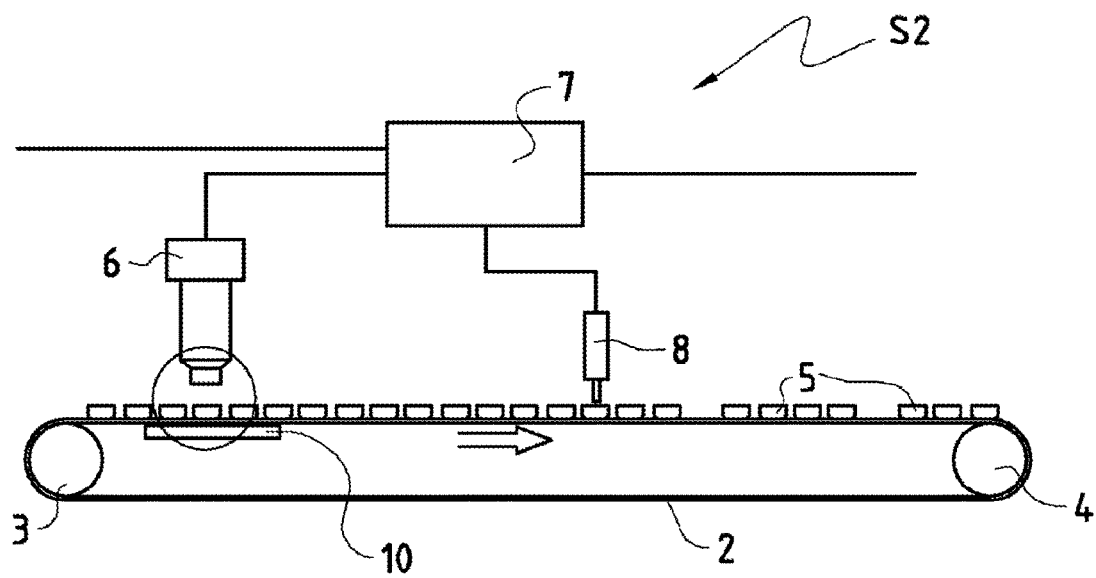
FIG. 3 shows schematically a block-like representation of a system for inspecting objects provided with a gas-barrier layer according to a second embodiment of the present invention, seen from the side.

FIG. 3 shows a system S2 which has practically the same structure as the system S1 already described. It likewise comprises a conveyor device (for example a conveyor belt 2) with the corresponding drive devices 3, 4, an image-recording module 6, a processing module 7 and an elimination module 8. In the system S2 too, the objects 5 provided with a gas-barrier layer that are to be inspected are guided by the conveyor device 2 past the image-recording module 6, so that a corresponding image can be created in the invisible light range. In the system S2 (which corresponds to a second embodiment of the present invention) too, the recorded images of the objects 5 provided with a gas-barrier layer that are to be inspected are transmitted to the processing module 7, where they are correspondingly evaluated and where, after the detection of faulty objects 5, those objects can be removed from the system S2 by the elimination module 8 by virtue of a corresponding elimination signal.

The above-described first embodiment of the present invention, that is to say the system S1 for inspecting objects provided with a gas-barrier layer, and the second embodiment of the present invention, that is to say the system S2 for inspecting objects provided with a gas-barrier layer, differ mainly in how the image is created in the invisible light range.

According to the first embodiment of the present invention, the objects 5 provided with a gas-barrier layer that are to be inspected are irradiated by external infrared radiation St. To that end there is provided an irradiation element 9 which is arranged in such a manner that it is able to irradiate the objects 5 to be inspected. The irradiation element 9 typically operates at low temperatures of approximately from 100° C. to 150° C. and is in the form of a black-body radiator. The operating temperature can also be higher if required by shortened exposure times.

Figure 2:
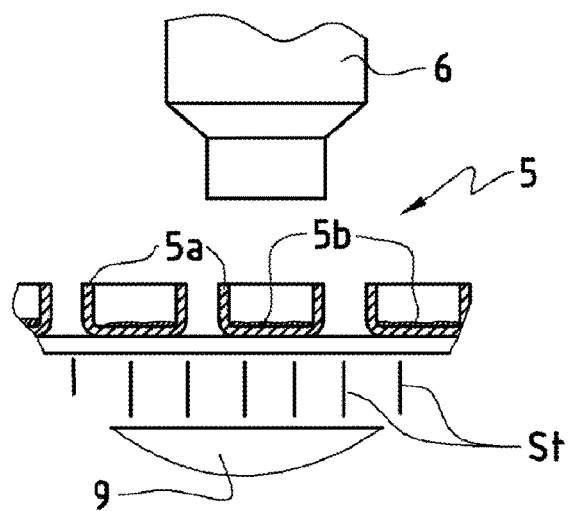
FIG. 2 shows an enlarged section from FIG. 1, where this section is shown by a circle.

FIG. 2 shows an enlarged section of FIG. 1, which is indicated in FIG. 1 by a circle. FIG. 2 shows the objects 5 provided with a gas-barrier layer that are to be inspected, in which the object body (the base layer) 5a and the gas-barrier layer 5b can clearly be seen. The base layers 5a of the objects 5 are conventionally made of a plastics material which is suitable for the production of screw caps, snap-on lids and similar objects. Typically it will be polypropylene (PP) or polyethylene (PE), but many other plastics materials are of course also conceivable. The gas-barrier layer 5b in the objects 5 will typically consist of an ethylene vinyl alcohol copolymer (EVOH) layer. As already mentioned, EVOH copolymers have outstanding properties which make them particularly suitable for the air-tight closing of containers. However, because only a gap-free gas-barrier layer 5b provides optimal protection from air, it is of the utmost importance to determine the faulty objects 5 as efficiently and reliably as possible.

Although the gas-barrier layer 5b is shown in FIG. 2 as a coating on the surface of the objects 5 to be inspected, it is also conceivable for the gas-barrier layer 5b to be in the form of an intermediate layer between two base layers 5a of a different material (or of several different materials). In addition, solutions are also conceivable in which not only one gas-barrier layer 5b but a plurality of gas-barrier layers 5b are provided.

As can be seen in FIG. 2, the objects 5 provided with a gas-barrier layer that are to be inspected are irradiated by the infrared radiation St, which is shown schematically here by straight lines. This infrared radiation is then reflected by the objects 5 provided with a gas-barrier layer, so that an image of each object 5 can then be created by the image-processing module 6, which is also shown. The material of the object body (or of the base layer) 5a and the material of the gas-barrier layer 5b can in particular be chosen in such a manner that they produce different images after irradiation by the infrared radiation St.

For example, the first material of the base layer 5a can be chosen in such a manner that it produces a reaction such as absorption, emission, scattering or reflection in a specific wavelength range (e.g. at 820 nm), while a different wavelength range (for example in the region of 890 nm) is emitted by the material of the gas-barrier layer 5b. In concrete terms, these different reactions normally manifest themselves as different transparencies of the individual layers. It has been shown, for example, that layers of EVOH copolymers have very low transparency (approximately less than 15%) at wavelengths between approximately 2850 and 3000 nm, while polypropylene and polyethylene are still very transparent in that range (approximately over 80%). Only at higher wavelengths (at approximately 3200 nm for polyethylene and at approximately 3300 nm for polypropylene) does the transparency of the remaining plastics layers also fall below the value of 5%. The individual layers can accordingly easily be detected by purposive irradiation, whereby it should be noted that other wavelength ranges can also be used. For example, it can also be shown that EVOH layers again have a much lower transparency at wavelengths of from approximately 6700 nm in comparison with the polyethylene or polypropylene layers.

An evaluation of the image of the object 5 by the processing module 7 can then very easily conclude, by the presence or absence of the reaction in predetermined wavelength ranges (that is to say differences in absorption, emission, scattering or reflection, for example on the basis of the different transparencies), whether the materials in question are present or whether regions in the objects 5 do not have a gas-barrier layer. In this manner, checking of the gas-barrier layer 5b can be carried out very efficiently, simply and reliably. In addition, because the evaluation algorithms in such an evaluation can be kept simple, a very high inspection rate can also be achieved, as a result of which the efficiency of the system as a whole can be increased.

Figure 4:
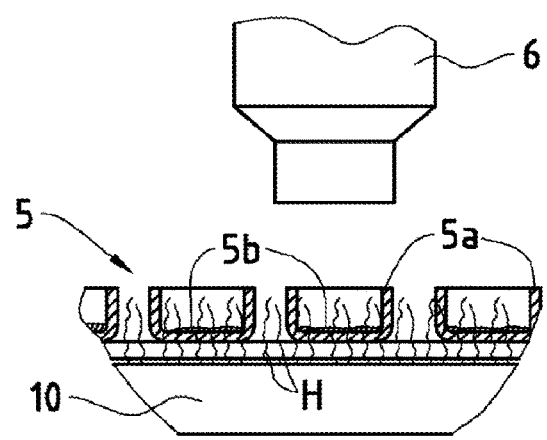
FIG. 4 shows an enlarged section from FIG. 3, where this section is shown by a circle.

FIG. 4, corresponding to the depiction in FIG. 2, shows a section of the system S2 according to the second embodiment of the present invention. In contrast to the system S1, the objects 5 provided with a gas-barrier layer that are to be inspected are not irradiated by the external infrared radiation St in the system S2, but a heating element 10 is provided, by means of which the objects 5 provided with a gas-barrier layer that are to be inspected are heated. The heat H is shown schematically in FIG. 4 by the wavy lines which rise upwards from the heating element 10. By heating the objects 5 provided with a gas-barrier layer that are to be inspected, the objects 5 develop a characteristic radiation in the infrared range. This phenomenon is already being used in so-called thermal cameras, which are used, for example, for evaluating the energy efficiency of buildings. In this case too, use is made of the fact that different materials develop different characteristic radiations, in particular that different materials emit radiation with different wavelength characteristics. If the material of the base layer 5a of the object 5 and the material of the gas-barrier layer 5b do not correspond, different wavelengths are determined by the image-recording module 6, as a result of which the faulty objects 5 can again be detected very easily by the processing module 7.

Apart from the features described above, the systems S1 and S2 according to the two embodiments of the present invention function in many respects like the conventional systems for inspecting workpieces in which cameras are used in the visible light range. Therefore, the corresponding details are omitted at this point, because they can very easily be understood by those skilled in the art.

However, it should be pointed out here that the present invention is not limited to the described embodiments. It will be readily apparent to a person skilled in the art that further developments and modifications are readily possible within the scope of the protected invention. For example, system elements can, if required, be replaced by different elements which perform the same or similar functions. Likewise, additional devices and/or elements can be provided, for example it is possible to provide a plurality of image-recording units, by virtue of which the objects to be inspected can be recorded from different sides. It is also possible to use a combination of external irradiation and heating in order to obtain more meaningful images. Finally, it would also be wholly conceivable to combine the above-described check in the invisible light range with a conventional check in the visible light range, in order to be able to carry out a complete inspection of the test pieces with a single system. Such measures and elements fall, however, within the scope of protection of the invention, which is defined by the following patent claims.

What is claimed is:

1. A method for inspecting objects (5) provided with a gas-barrier layer which consist of at least one base layer (5a) of a first material and at least one gas-barrier layer (5b) of a second material, wherein an image of each object (5) is recorded by an image-recording module (6) and is processed by a processor (7) in such a manner that faulty objects (5) are detected and eliminated, the method comprising the steps of
creating and recording the image of each object (5) by the image-recording module (6) in the invisible light range,
examining the recorded image by the processor (7), and
determining a presence, an absence, a thickness and an evenness of the gas-barrier layer (5b) based on the image,
wherein the image-recording module (7) operates within a range of wavelengths of 2.5 µm to 5.1 µm.

2. The method according to claim 1, wherein the first material of the base layer (5a) and the second material of the gas-barrier layer (5b) are chosen in such a manner that they produce different images in the invisible light range.

3. The method according to claim 1, wherein the image of the object (5) is examined at predetermined wavelengths, wherein those wavelengths are chosen in dependence on the first material of the base layer (5a) and on the second material of the gas-barrier layer (5b).

4. The method according to claim 1, wherein the image-recording module (6) is a cooled IR camera.

5. The method according to claim 1, further comprising the steps of determining that an object (5) is faulty, and
eliminating the faulty object (5) by an elimination module (8) based on a signal from the processor (7).

6. The method according to claim 1, further comprising the step of transporting the objects (5) by a conveyor device (2) past the image-recording module (6) in such a manner that an image of each object (5) is recorded.

7. The method according to claim 6, wherein the conveyor device (2) guides the objects past the image-recording module (6) continuously.

8. The method according to claim 1, further comprising the step of irradiating the objects (5) by an irradiation element (9) with infrared radiation (St).

9. The method according to claim 1, further comprising the step of heating the objects (5) by a heating element (10) in such a manner that they develop a characteristic radiation in the infrared range.

10. The method according to claim 1, wherein the first material of the base layer (5a) consists of at least one of polypropylene and polyethylene and the second material of the gas-barrier layer (5b) consists of at least one of ethylene vinyl acetate (EVA) and ethylene vinyl alcohol copolymer (EVOH).

11. A system for inspecting objects (5) provided with a gas-barrier layer which consist of at least one base layer (5a) of a first material and at least one gas-barrier layer (5b) of a second material, the system comprising, an image-recording module (6) and a processor (7) for detecting and eliminating faulty objects (5), wherein the image-recording module (6) is configured to record an image of each object (5) in the invisible light range and wherein the processor (7) is configured to examine the recorded image and to determine a presence, an absence, a thickness and an evenness of the gas-barrier layer (5b) based on the image, wherein the image-recording module (7) operates within a range of wavelengths of 2.5 μm to 5.1 μm.

12. The system according to claim 11, wherein the first material of the base layer (5a) and the second material of the gas-barrier layer (5b) are chosen in such a manner that they produce different images in the invisible light range.

13. The system according to claim 11, wherein the image-recording module (7) is a cooled IR camera.

14. The system according to claim 11, further comprising a conveyor device (2) which guides the objects (5) past the image-recording module (6) continuously.

15. The system according to claim 11, further comprising an elimination module (8) by means of which faulty objects (5) can be eliminated on the basis of a signal from the (7).

16. The system according to claim 11, further comprising an irradiation element (9) by means of which the objects (5) can be irradiated by the infrared radiation (St).

17. The system according to claim 11, further comprising a heating element (10) by means of which the objects (5) can be heated in such a manner that they develop a characteristic radiation in the infrared range.

* * * * *